(12) United States Patent
Gonzales

(10) Patent No.: US 8,235,050 B2
(45) Date of Patent: Aug. 7, 2012

(54) APPARATUS AND METHOD FOR SECURING UVULA

(75) Inventor: Donald Gonzales, San Antonio, TX (US)

(73) Assignee: MimOSA Medical, Inc., Needham, MA (US)

( * ) Notice: Subject to any disclaimer, the term of this patent is extended or adjusted under 35 U.S.C. 154(b) by 938 days.

(21) Appl. No.: 12/209,976

(22) Filed: Sep. 12, 2008

(65) Prior Publication Data
US 2009/0084389 A1 Apr. 2, 2009

Related U.S. Application Data

(60) Provisional application No. 60/972,500, filed on Sep. 14, 2007.

(51) Int. Cl.
*A61F 5/56* (2006.01)

(52) U.S. Cl. .......................................... 128/848

(58) Field of Classification Search ............... 128/848
See application file for complete search history.

(56) References Cited

U.S. PATENT DOCUMENTS

| 6,193,716 B1 | 2/2001 | Shannon ................. 606/45 |
| 7,845,356 B2 * | 12/2010 | Paraschac et al. ........... 128/848 |
| 2006/0207607 A1 | 9/2006 | Hirotsuka et al. ........... 128/848 |
| 2007/0102004 A1 | 5/2007 | Nelson et al. ............... 128/848 |

OTHER PUBLICATIONS

International Search Report and Written Opinion, issued in International Application No. PCT/US2008/076221, dated Nov. 17, 2008.

* cited by examiner

*Primary Examiner* — Patricia Bianco
*Assistant Examiner* — Victoria J Hicks
(74) *Attorney, Agent, or Firm* — Bingham McCutchen LLP

(57) ABSTRACT

A method and apparatus for securing a uvula to a soft palate. The uvula may be attached to either the nasopharyngeal side or the oral side of the soft palate with a uvula securement device. The uvula may be secured to the nasopharyngeal side of the soft palate with a suture.

20 Claims, 15 Drawing Sheets

ABSTRACT## APPARATUS AND METHOD FOR SECURING UVULA

CROSS-REFERENCE TO RELATED APPLICATIONS

This application claims priority to U.S. Provisional Patent Application Ser. No. 60/972,500, filed Sep. 14, 2007, the entire contents of which are expressly incorporated herein by reference.

FIELD OF THE INVENTION

The present disclosure relates generally to apparatus and methods for securing a patient's uvula. The present disclosure relates more specifically to apparatus and methods for securing a patient's uvula to the nasopharyngeal or oral side of the soft palate.

BACKGROUND INFORMATION

In certain instances, it may be desirable to secure a patient's uvula as a result of medical or environmental conditions. One such example is when a patient snores excessively so that the uvula becomes traumatized and elongated.

Snoring is a prevalent condition in our society, with an incidence rate as high as 20% of the adult population. Snoring can cause not only difficulty in social environments, but also can be the harbinger of more serious health problems such as obstructive sleep apnea. Snoring can be caused by the oscillation of the oropharyngeal soft tissue during the inspiratory phase of breathing during sleep. Increased negative intrathoracic pressure can lead to collapse of the soft tissue causing apposition of the soft palate and uvula with the surrounding structures. The uvula, as time progresses, can become hypertrophic with increased fat content. The enlarged uvula can then cause worsening snoring, which further affects the uvula and creates a cycle of problems.

Snoring treatment can be first targeted on weight loss to reduce the soft tissue in the oropharynx. Weight loss is often a difficult challenge for these patients and the time required for a change in snoring habits are often not well tolerated. It can therefore be desirable to secure the patient's uvula to relieve the snoring symptoms. If adequate weight loss is achieved, the uvula can be released so that it returns to its normal position; or, if necessary, the uvula can be permanently secured to relieve the snoring symptoms.

While snoring is provided as one example of a medical condition that may warrant securement of the patient's uvula, other medical conditions warranting securement also exist such as obstructive sleep apnea, velopharyngeal insufficiency and nasopharyngeal stenosis.

SUMMARY

Certain embodiments of the present disclosure comprise a method of securing a uvula. The method may comprise: providing a securement device or a suture; positioning the uvula so that the uvula is proximal to a nasopharyngeal side of a soft palate; and securing the uvula to the nasopharyngeal side of a soft palate with either the securement device or the suture. The method may also comprise providing a securement device; positioning the uvula so that the uvula is proximal to an oral side of a soft palate; and securing the uvula to the oral side of the soft palate with the securement device. Other exemplary embodiments may comprise providing a securement device; engaging the securement device with the uvula; positioning the uvula so that the uvula is proximal to a soft palate; and engaging the securement device with the soft palate to secure the uvula to the soft palate. In still other exemplary embodiments the uvula may be positioned proximal to the nasopharyngeal side of the soft palate or the oral side of the soft palate.

In certain exemplary embodiments, the securement device may engage the posterior portion of the uvula, while in other embodiments, it may engage the nasopharyngeal side of the soft palate. In certain embodiments, the securement device may initially engage the uvula and subsequently engage the soft palate, while in other embodiments, the securement device may initially engage the soft palate and subsequently engage the uvula.

In certain exemplary embodiments, the securement device may comprise a central portion having a first side with a first barb, and securing the securement device to the uvula may comprise penetrating the uvula with the first barb. In certain embodiments, securing the securement device to the soft palate comprises penetrating the soft palate with the first barb. In certain exemplary embodiments, the central portion of the securement device may comprise a second side with a second barb, and securing the securement device to the soft palate comprises penetrating the soft palate with the second barb.

In certain exemplary embodiments, securing the securement device to the uvula may comprise providing an attachment tool comprising a first shaft with a first end having a first slot, a second shaft with a second end, and an actuator configured to move the second end closer to the first end. Securing the securement device to the uvula may comprise placing the securement device in the first slot; positioning the attachment tool so that the uvula is positioned between the first end and the second end; actuating the actuator so that the second end engages the uvula and the uvula engages the first end; actuating the actuator to move the second end away from the first end; and moving the attachment tool so that the securement device slides out of the first slot.

In other exemplary embodiments, securing the securement device to the soft palate may comprise: providing a securement tool comprising a handle, a shaft, and a curved end distal to the handle; utilizing the securement tool to position the uvula so that the securement device is proximal to the nasopharyngeal side of the soft palate; engaging the curved end with the uvula and exerting a force on the uvula in the direction of the nasopharyngeal side of the soft palate to secure the securement device the nasopharyngeal side of the soft palate.

Other exemplary embodiments comprise an apparatus for securing a uvula. The apparatus may comprise: a main body having a first side and a second side; a first extension extending from first side of the main body, wherein the first extension has a first end distal from the main body; and a first barb proximal to the first end of the first extension. Other exemplary embodiments may comprise a second extension extending from the second side of the main body, wherein the second extension has a second end distal from the main body, and a second barb that is proximal to the second end of the second extension.

Certain embodiments comprise a method of securing a uvula, the method comprising: providing a securement device; positioning the uvula so that the uvula is proximal to a side of a soft palate; and securing the uvula to the nasopharyngeal side of a soft palate with either the securement device. The uvula may be positioned proximal to the nasopharyngeal or oral side of the soft palate. In certain embodiments, the securement device comprises a barb. The securement device comprises may comprise a suture and a suture anchor member.

In certain embodiments, the securement device is selected from the group consisting of a staple, tack, rivet and suture comprising a bio-absorbable or a non-bioabsorbable material.

In certain embodiments, securing the securement device to the uvula comprises: providing an attachment tool comprising: a first shaft with a first end having a first slot; a second shaft with a second end; and an actuator configured to move the second end closer to the first end. Embodiments may also comprise placing the securement device in the first slot; positioning the attachment tool so that the uvula is positioned between the first end and the second end; actuating the actuator so that the second end engages the uvula and the uvula engages the first end; actuating the actuator to move the second end away from the first end; and moving the attachment tool so that the securement device slides out of the first slot.

In certain embodiments, securing the securement device to the soft palate comprises: providing a securement tool comprising a handle, a shaft, and a curved portion distal to the handle; utilizing the securement tool to position the uvula so that the securement device is proximal to the nasopharyngeal side of the soft palate; engaging the curved portion with the uvula and exerting a compressive force on the uvula to secure the securement device the nasopharyngeal side of the soft palate. In certain embodiments, exerting the compressive force on the uvula comprises extending an actuation member from the securement tool.

Certain embodiments comprise a method of securing a uvula, the method comprising: providing a securement device; engaging the securement device with the uvula; positioning the uvula so that the uvula is proximal to a soft palate; and engaging the securement device with soft palate to secure the uvula to the soft palate. In certain embodiments, the uvula is positioned proximal to the nasopharyngeal side of the soft palate. In other embodiments, the uvula is positioned proximal to the oral side of the soft palate. In certain embodiments, the securement device engages the posterior portion of the uvula. The securement device may engage the nasopharyngeal side of the soft palate. In certain embodiments, the securement device initially engages the uvula and subsequently engages the soft palate. In certain embodiments, the securement device initially engages the soft palate and subsequently engages the uvula.

In certain embodiments, the securement device comprises a central portion having a first side with a first barb, and securing the securement device to the uvula comprises penetrating the uvula with the first barb. In certain embodiments, securing the securement device to the soft palate comprises penetrating the soft palate with the first barb.

In certain embodiments, the central portion of the securement device comprises a second side with a second barb and securing the securement device to the soft palate comprises penetrating the soft palate with the second barb.

Certain embodiments comprise an apparatus for securing a uvula, the apparatus comprising: a main body having a first side and a second side; a first extension extending from first side of the main body, wherein the first extension has a first end distal from the main body; and a first barb proximal to the first end of the first extension. Certain embodiments comprise a second extension extending from the second side of the main body, wherein the second extension has a second end distal from the main body; and a second barb proximal to the second end of the second extension.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF EXEMPLARY EMBODIMENTS

Figure 1:
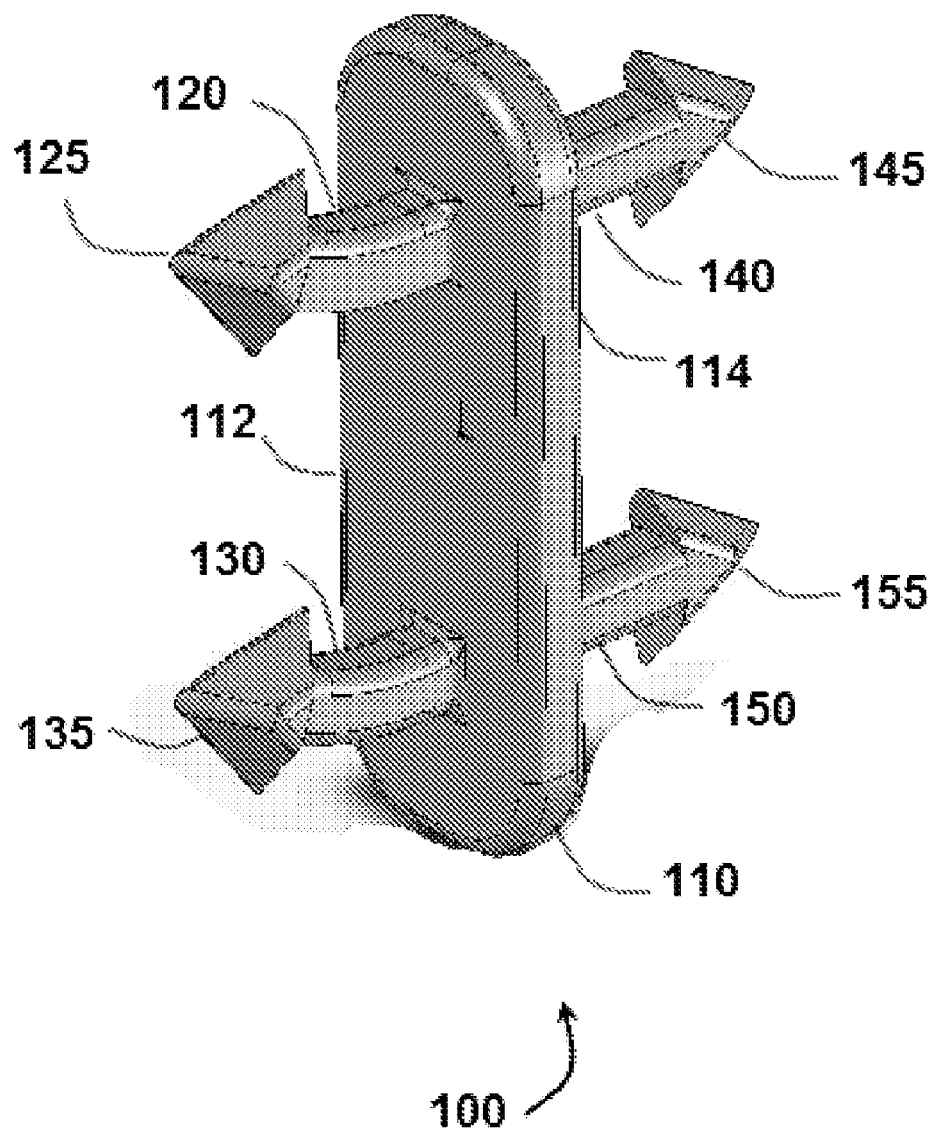
FIG. 1 illustrates a perspective view of an exemplary embodiment of a uvula securement device.
Figure 2:
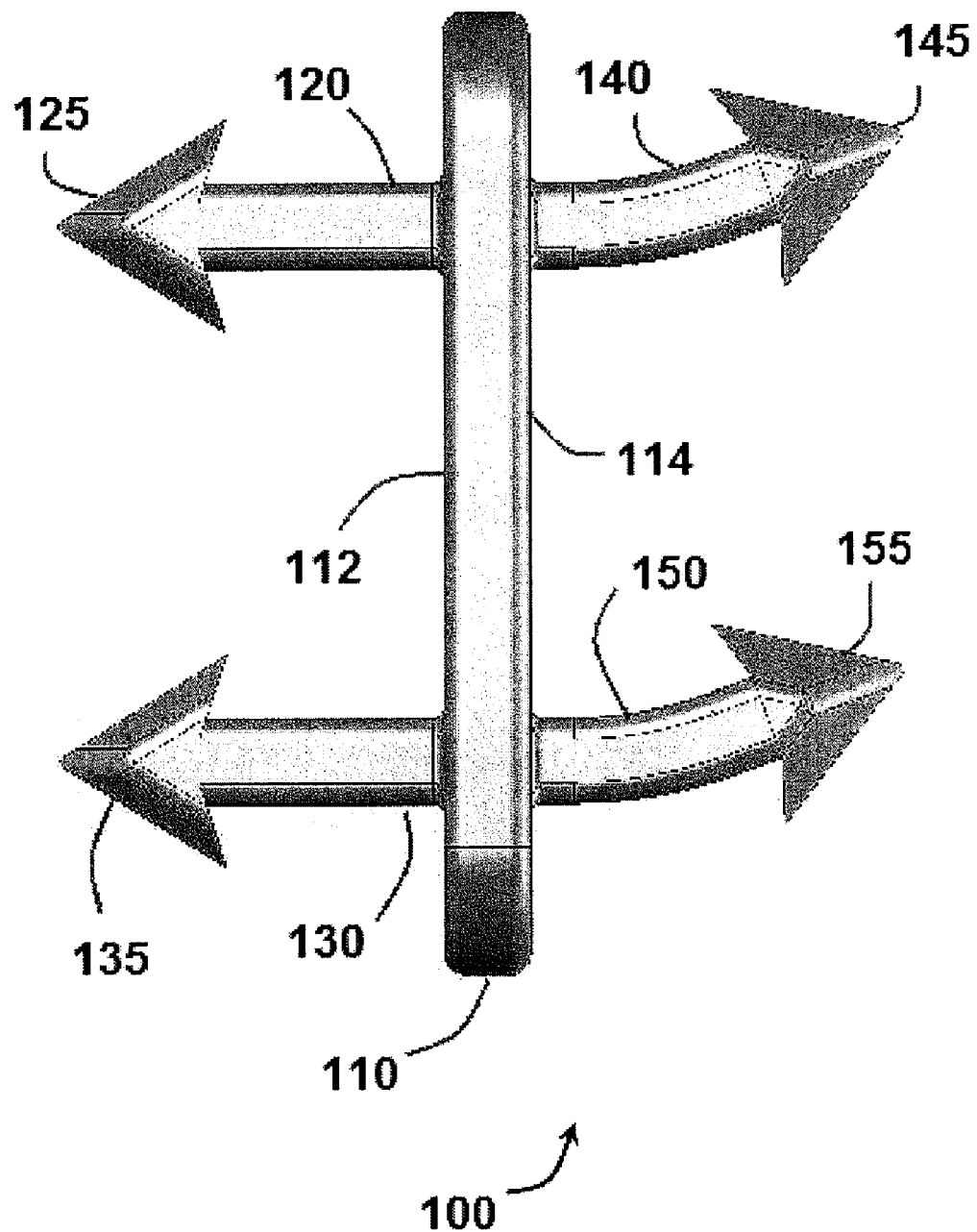
FIG. 2 illustrates an side view of the exemplary embodiment of FIG. 1.
Figure 3:
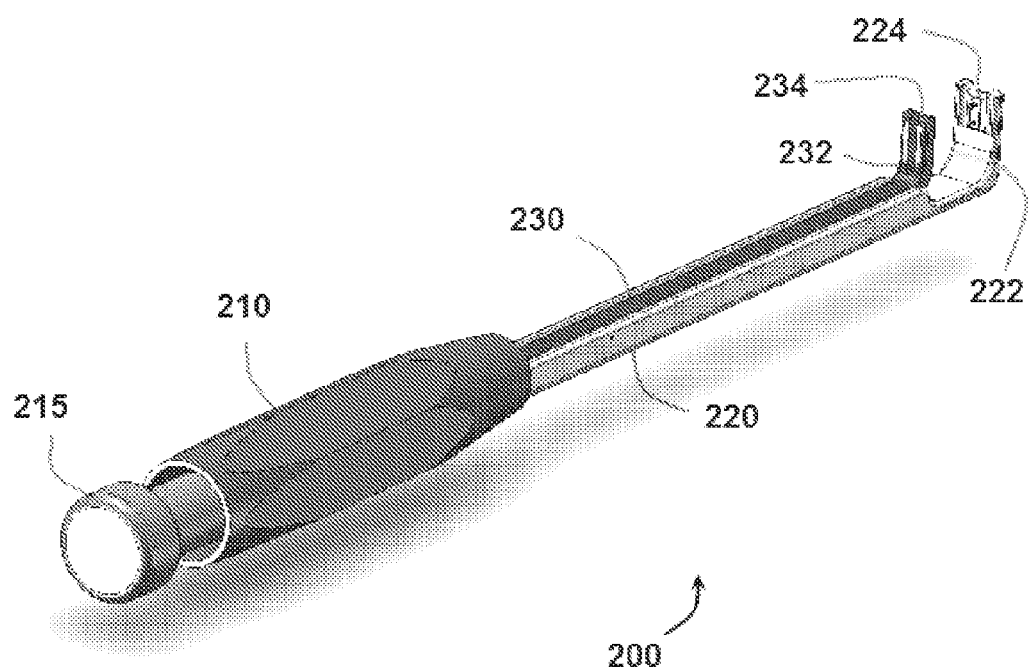
FIG. 3 illustrates a perspective view of an exemplary embodiment of a tool used to install a uvula securement device.

Referring initially to the exemplary embodiment shown in FIGS. 1 and 2, a uvula securement device (USD) 100 comprises a central portion 110 with a first side 112 and a second side 114. A pair of extensions 120 and 130 extend from a first side 112, while a pair of extensions 140 and 150 extend from second side 114. Extension 120 comprises a barb 125 at the end of extension 120 that is distal from first side 112, and extension 130 comprises a barb 135 at the end distal from side 112.

Similarly, a pair of extensions 140 and 150 extend from a second side 114 of central portion 110. Extension 140 comprises a barb 145 at the end of extension 140 that is distal from second side 114, and extension 150 comprises a barb 155 at the end of extension 150 that is distal from second side 114.

Referring now to the exemplary embodiment in FIGS. 3-7, an attachment tool 200 comprises a handle 210, an actuator 215, an external shaft 220 and an internal shaft 230. External shaft 220 comprises an end 222 with a slot 224 configured to receive USD 100. Internal shaft 230 comprises an end 232 with a slot 234 configured to receive USD 100. In the exemplary embodiment shown, slot 224 is configured to receive extensions 120 and 130 in a manner so that USD 100 is retained in slot 224. Specifically, barbs 125 and 135 are disposed on one side of slot 224 and central portion 110 is disposed on the opposite side of slot 224, so that USD 100 is retained in slot 224 and end 222 of attachment tool 200. In the exemplary embodiment shown, slot 234 is configured so that barbs 145 and 155 may extend through slot 234 if desired.

Figure 4:
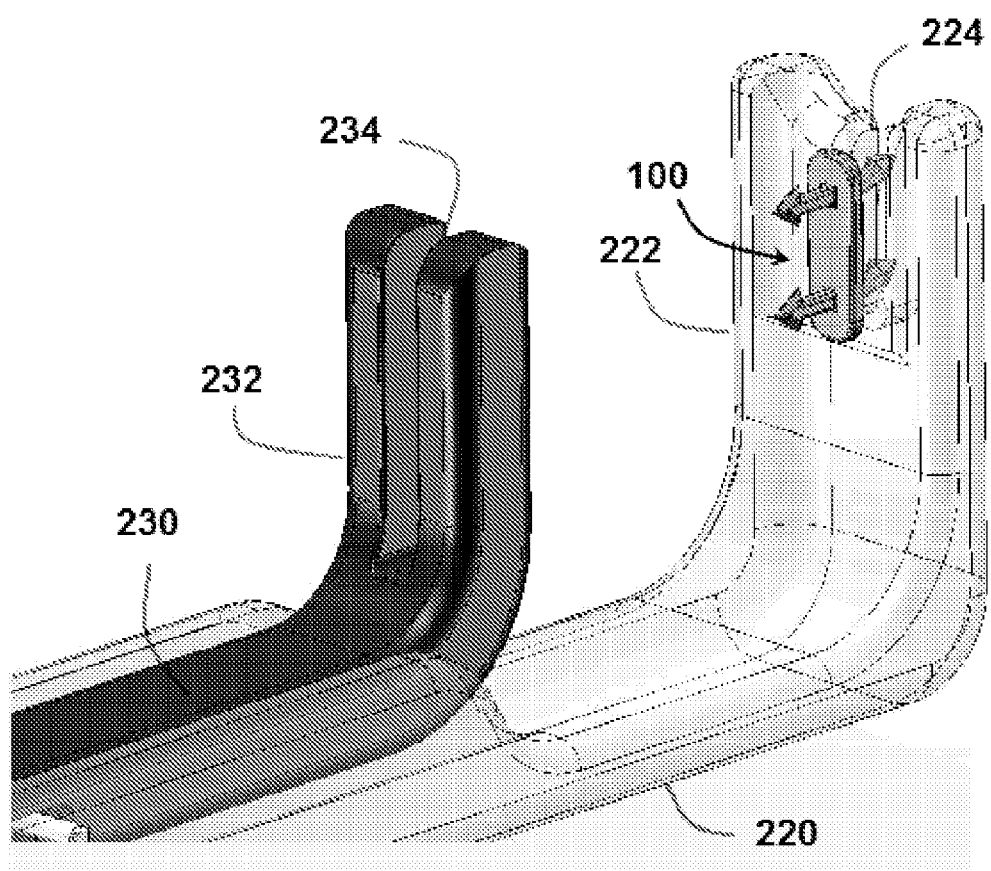
FIG. 4 illustrates detailed view of the embodiment of FIG. 3.
Figure 5:
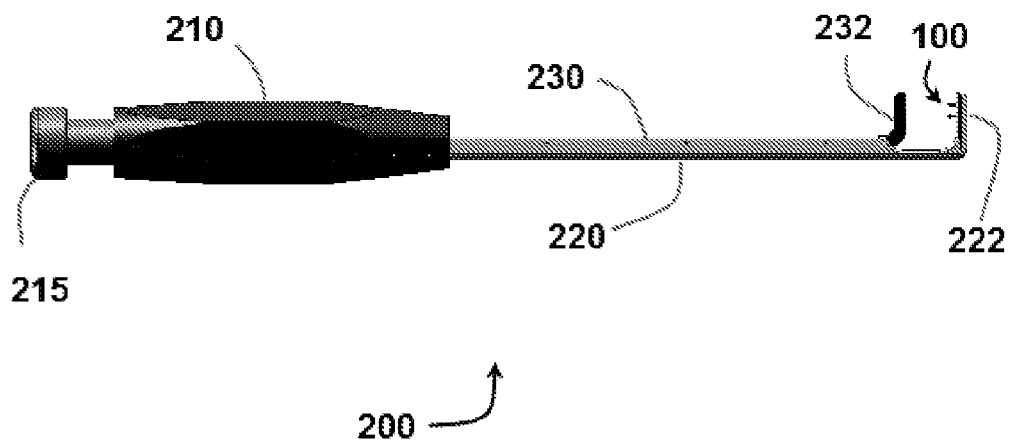
FIG. 5 illustrates side view of the embodiment of FIG. 3.
Figure 6:
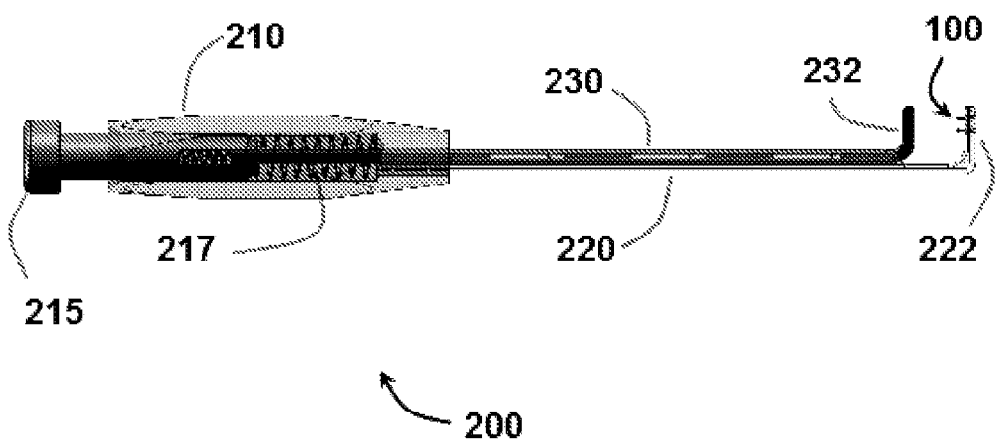
FIG. 6 illustrates a partial section view of the embodiment of FIG. 3 in an open position.
Figure 7:
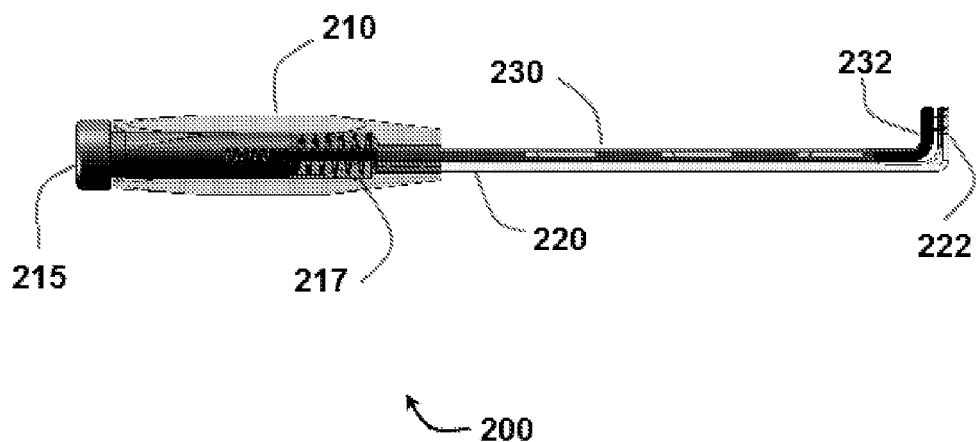
FIG. 7 illustrates a partial section view of the embodiment of FIG. 3 in a closed position.

As shown in FIGS. 4-6, a gap 240 exists between end 222 and end 232 when attachment tool 200 is in the extended position. In the exemplary embodiment shown in FIG. 7, gap 240 can be decreased (or eliminated) as actuator 215 is pushed toward handle 210. In the partial section views of FIGS. 6 and 7, a biasing member 217 is visible. Biasing member 217 biases actuator 215 (which is coupled to internal shaft 230) away from handle 210. As a result, biasing member 217 biases internal shaft 230 and end 222 away from end 232 so that gap 230 is increased. However, an operator can overcome the force exerted by biasing member 217 and move actuator 215 towards handle 210. This action moves end 222 towards end 232 and decreases gap 230.

Figure 8:
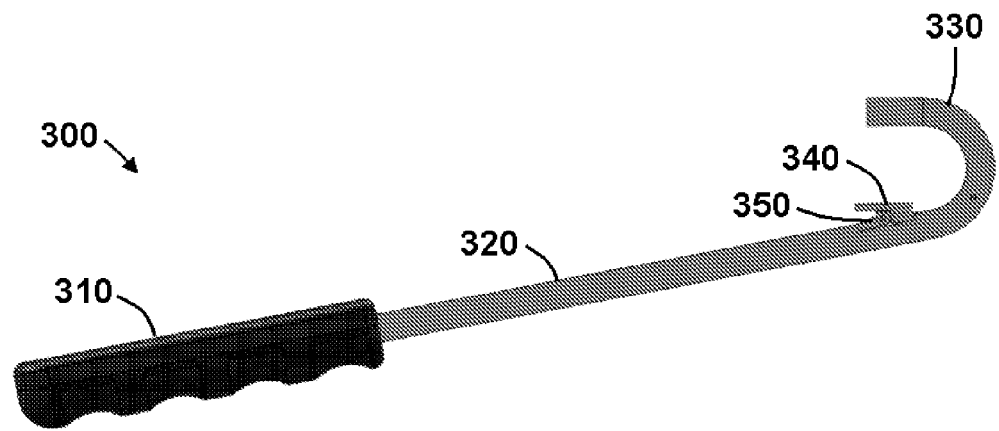
FIG. 8 illustrates a side view of an embodiment of a tool used to install a uvula securement device.

Referring now to FIG. 8, one embodiment of a securement tool 300 comprises a handle 310, a shaft 320 and a curved portion 330. Securement tool 300 also comprises an actuation member 340 that can extend from or retract into securement tool 300 (in this embodiment, from the portion where shaft 320 transitions into curved portion 330). Actuation member 340 can be actuated by any suitable mechanism (for example, a trigger, button, cam, slide, etc.). In certain embodiments, the mechanism used to move actuation member 340 is proximal to handle 310 so that a user can hold securement tool 300 and actuate actuation member 340 with one hand. As explained further below, attachment tool 200 and securement tool 300 can be used to attach USD 100 to a patient's uvula and secure the uvula to a proximal surface of the patient (for example, the nasopharyngeal side of the soft palate).

Figure 9:
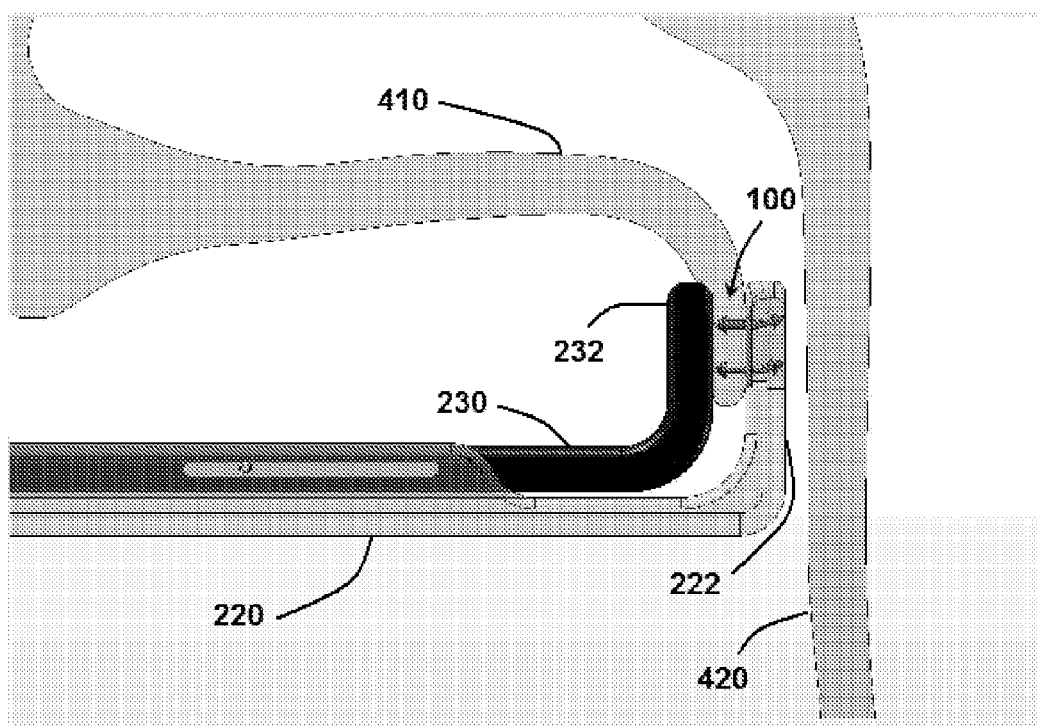
FIG. 9 illustrates a side view of the embodiment of FIG. 1 being secured to a uvula.

As shown in the exemplary embodiment of FIG. 9, USD 100 can be attached to a patient's uvula 400. In certain exemplary embodiments, USD 100 is attached to the posterior portion of a patient's uvula 400 (i.e., the portion of the uvula closest to a patient's throat 420). In this embodiment, USD 100 is placed in slot 224 of attachment tool 200 (in the manner shown in FIG. 4) and then positioned behind uvula 400. Attachment tool 200 is positioned so that uvula 400 is placed between ends 232 and 222. Actuator 215 can then be moved towards handle 210 (not visible in FIG. 9) so that end 232 engages uvula 400 and uvula 400 engages barbs 145 and 155 of USD 100. In the position shown in FIG. 9, actuator 215 has been moved towards handle 210 sufficiently for barbs 145 and 155 to pierce uvula 400. Actuator 215 can then be released so that biasing member 217 (not shown in FIG. 9) moves actuator 215 away from handle 210. In addition, end 232 will move away from end 222 so that uvula 400 is no longer captured between ends 232 and 222.

Figure 10:
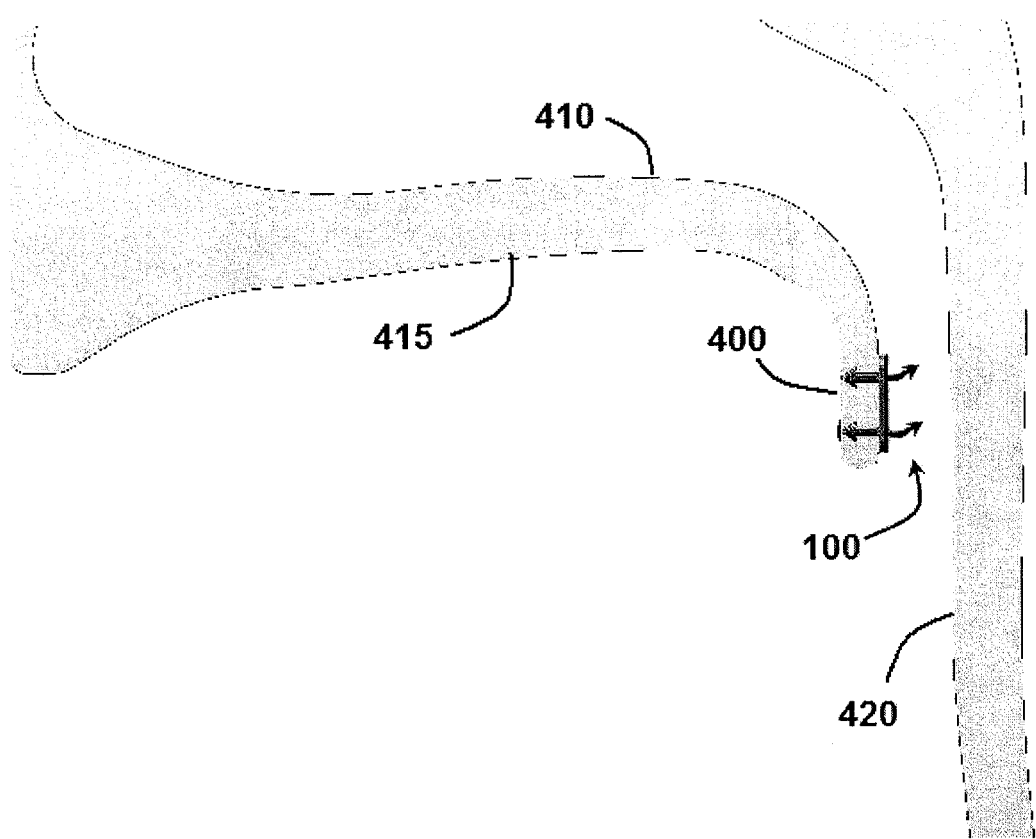
FIG. 10 illustrates a side view of the embodiment of FIG. 1 secured to a uvula.

Attachment tool 200 can then be moved (down in the orientation shown in FIG. 9) so that extensions 140 and 150 are allowed to slide out of slot 222 of end 224. As a result, USD 100 is attached to the posterior portion of uvula 400 in the manner shown in FIG. 10. Securement tool 300 can then be positioned so that curved end 330 engages uvula 400 and positions uvula 400 in the manner shown in FIG. 11. As shown in FIG. 12, securement tool 300 can then be manipulated so that actuation member 340 extends from securement tool 300. In this view, a linkage 350 supports actuation member 340 as it extends from securement tool 300 and engages the soft palate 415. Further extension of actuation member 340 compresses the repositioned uvula 400 to the soft pallet 415 so that barbs 125 and 135 (not labeled for purposes of clarity) pierce the nasopharyngeal side 410 of soft palate 415.

In this manner, uvula 400 can be attached to the nasopharyngeal side 410 of the soft palate 415 to provide relief from medical conditions including, for example, snoring. In certain exemplary embodiments, USD 100 can be made from a material that is not bio-degradable or bio-absorbable so that the attachment of uvula 400 is relatively permanent. In other exemplary embodiments, USD 100 can be made from a material that will eventually dissolve (such as a bio-degradable or bio-absorbable material) so that the attachment of uvula 400 is not permanent. For example, uvula 400 could be attached for a period of time until the patient loses a desired amount of weight.

Figure 13:
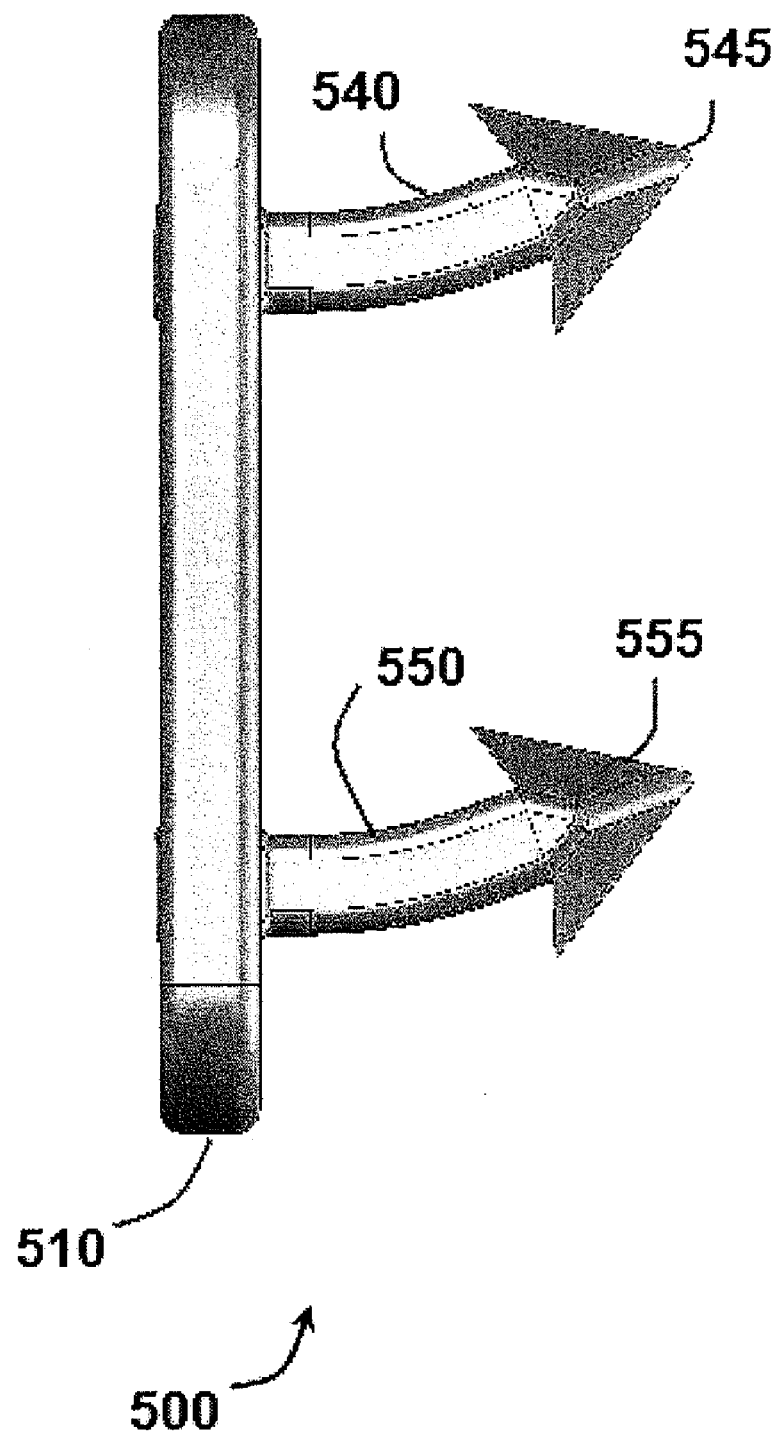
FIG. 13 illustrates a side view of a second exemplary embodiment of a uvula securement device.
Figure 14:
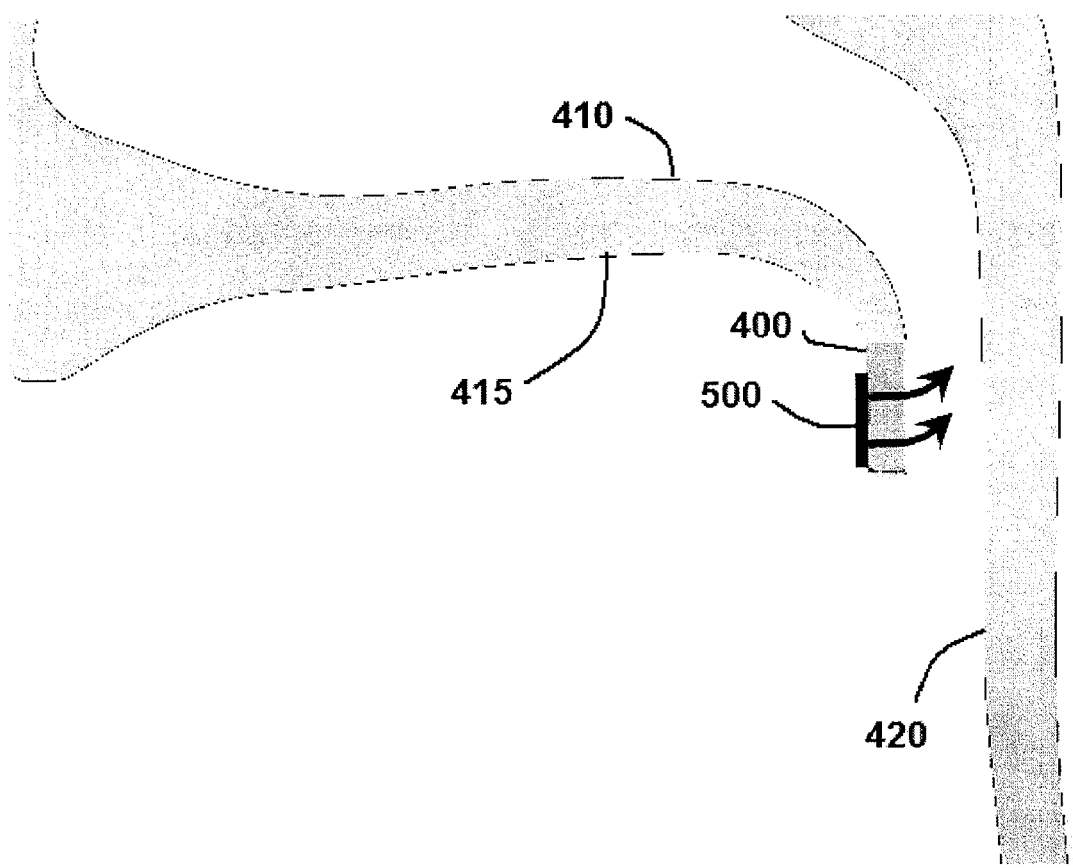
FIG. 14 illustrates a side view of the embodiment of FIG. 13 secured to a uvula.

Referring now to FIGS. 13 and 14, an alternative embodiment of a uvula securement device (USD) 500 comprises a main body 510 with a pair of extensions 540 and 550 extending from main body 510. Extension 540 comprises a barb 545 and extension 550 comprises a barb 555, each distal from main body 510. As shown in FIG. 14, extensions 540 and 550 are of sufficient length to penetrate through uvula 400 so that barbs 545 and 555 extend out of the posterior portion of uvula 400 when main body 510 is placed against the anterior portion of uvula 400 (i.e., the portion of uvula 400 that is distal from the patient's throat 420). USD 500 may be secured to uvula 400 as shown in FIG. 13 with the assistance of a device similar to attachment tool 200.

Figure 11:
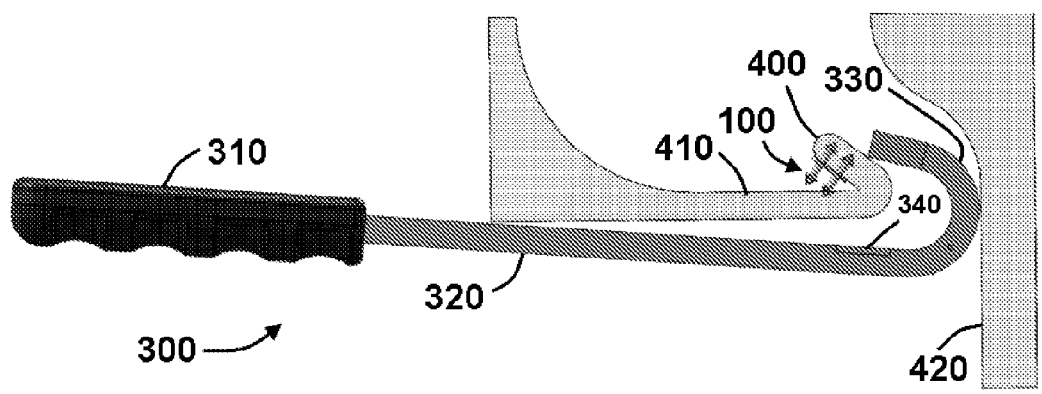
FIG. 11 illustrates a side view of the embodiment of FIG. 1 as the uvula is repositioned.
Figure 12:
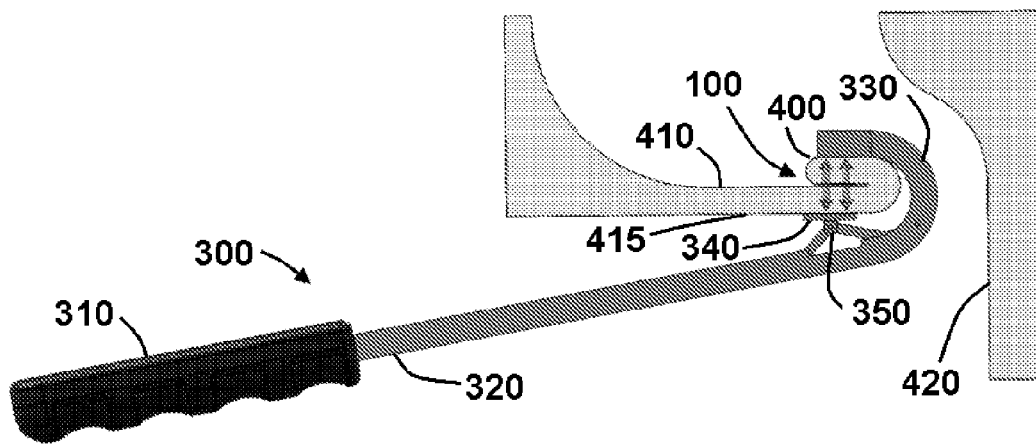
FIG. 12 illustrates a side view of the embodiment of FIG. 1 secured to the nasopharyngeal side of the soft palate.

After USD 500 has been secured to uvula 400 in the manner shown in FIG. 14, uvula 400 can be positioned proximal to the nasopharyngeal side 410 of the soft palate 415 in a manner similar to that shown in FIG. 11. Uvula 400 can then be secured to the nasopharyngeal side 410 of the soft palate 415 in a manner similar to that shown in FIG. 12.

Figure 15:
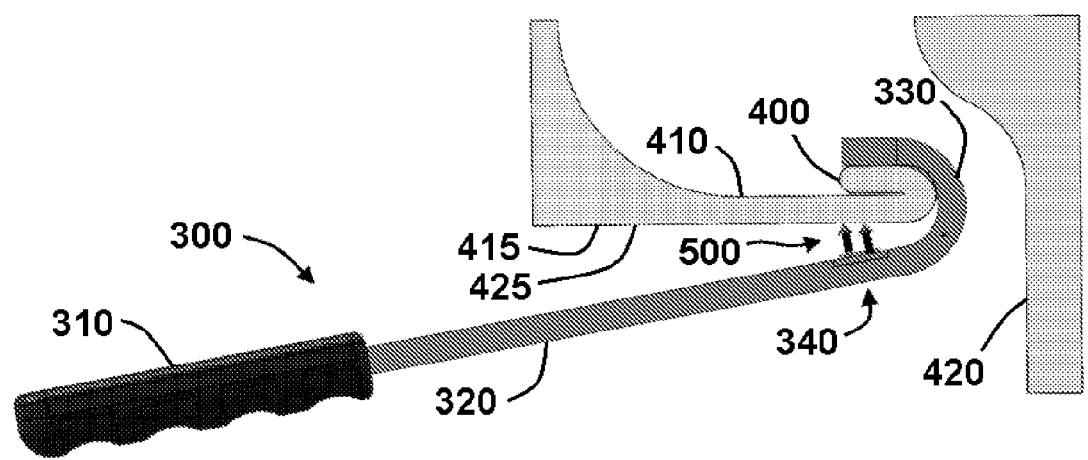
FIG. 15 illustrates a side view of side view of the embodiment of FIG. 13 being secured to the soft palate.
Figure 16:
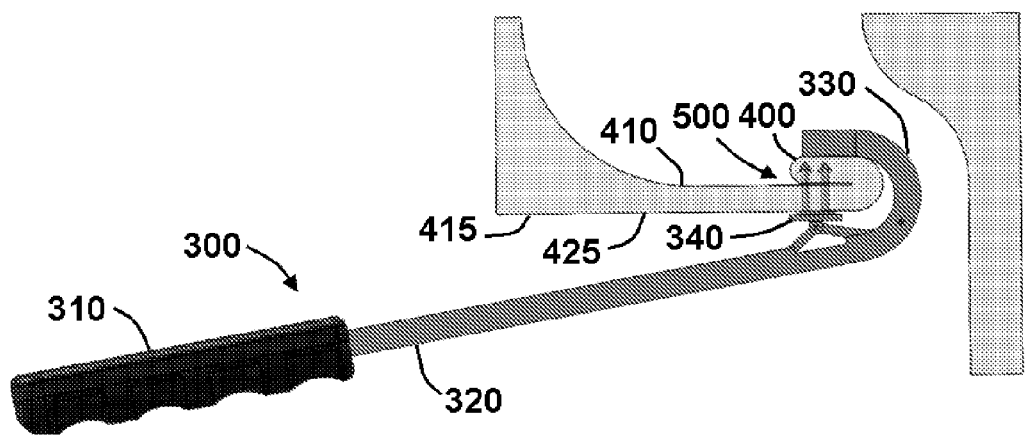
FIG. 16 illustrates a side view of the embodiment of FIG. 13 securing the uvula to the nasopharyngeal side of the soft palate.

Other embodiments may comprise variations in the configuration of the uvula securement device or the location within the patient's mouth of the initial installation of the uvula securement device. In the embodiment shown in FIGS. 15 and 16, USD 500 is initially coupled to securement tool 300 (e.g. to actuation member 340 in the embodiment shown). USD 500 can be positioned proximal to an oral side 425 of soft palate 415, and curved portion 330 of securement tool 300 can be used to position uvula 400 proximal to nasopharyngeal side 410 of the soft palate 415. Securement tool 300 can be actuated in the manner previously described in the embodiment shown in FIG. 12. Such action compresses the repositioned uvula 400 to the soft pallet 415 so that barbs 545 and 555 pierce the nasopharyngeal side of 410 of the soft pallet 415 and the uvula 400, securing it in place.

Figure 17:
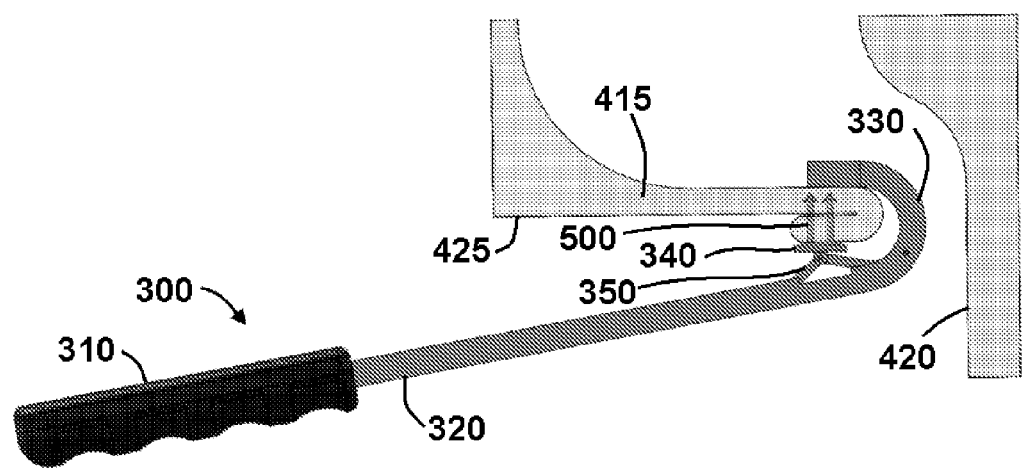
FIG. 17 illustrates a side view of the embodiment of FIG. 13 securing the uvula to the oral side of the soft palate.

In other exemplary embodiments, a uvula securement device can be used to secure a uvula to the oral side of a patient's soft palate. Referring to the exemplary embodiment shown in FIG. 17, USD 500 is shown securing uvula 400 to oral side 425 of soft palate 415. In this embodiment, USD 500 is initially secured to uvula 400 (e.g., using securement tool 200), which is then positioned proximal to oral side 425 before USD 500 is secured to oral side 425 by actuating securement tool 300 in a manner similar to that described in the description of FIG. 12. In other exemplary embodiments, uvula 400 is initially positioned proximal to oral side 425 and then USD 500 is used to secure uvula 400 to oral side 425.

Figure 18:
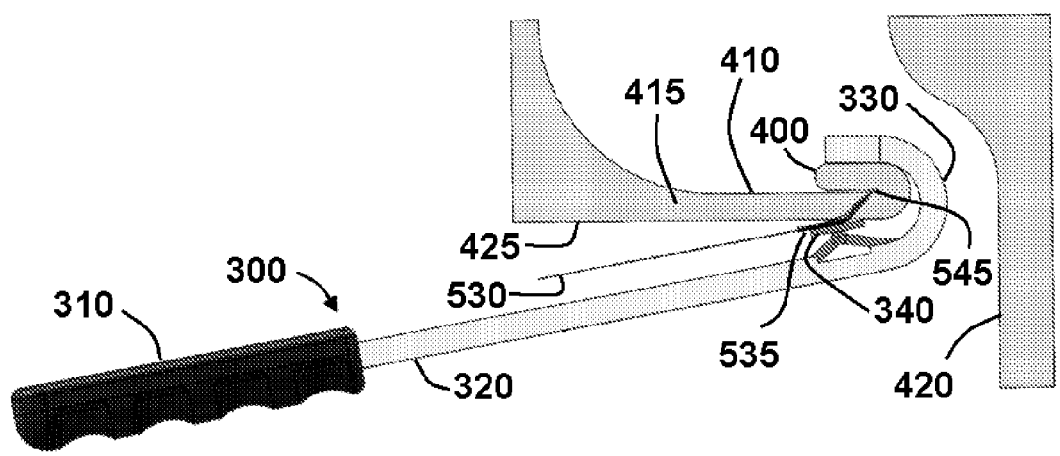
FIG. 18 illustrates a side view of a suture being installed to secure the uvula to the nasopharyngeal side of the soft palate.
Figure 19:
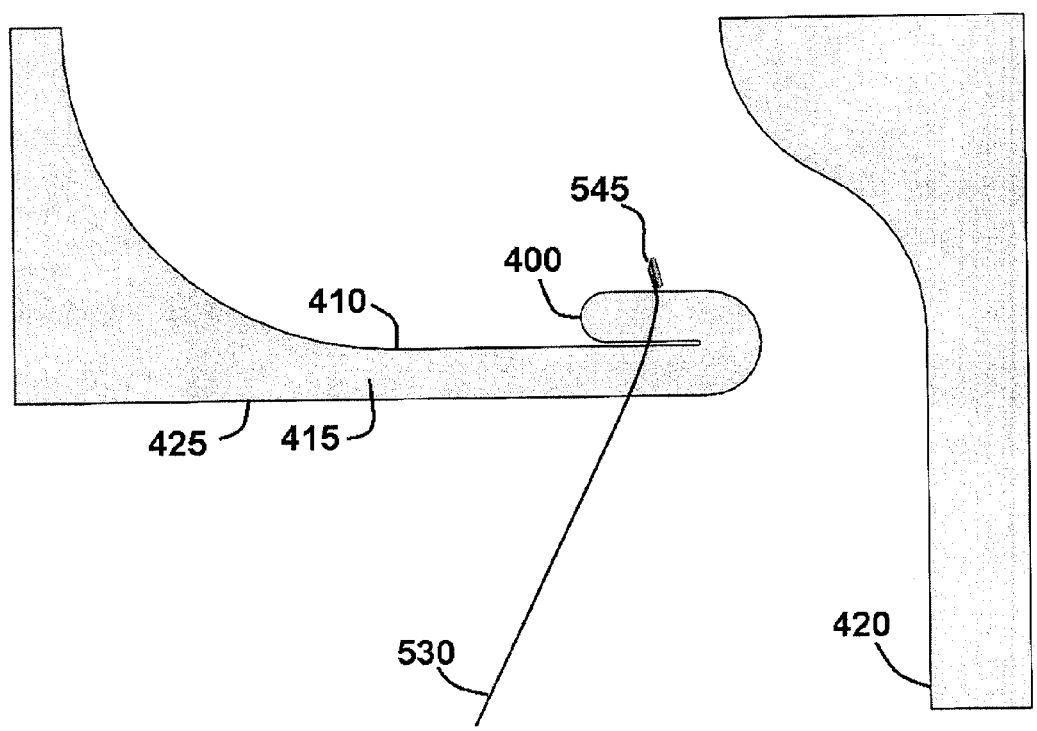
FIG. 19 illustrates a side view of a suture securing the uvula to the nasopharyngeal side of the soft palate

As shown in FIGS. 18 and 19, in other exemplary embodiments a uvula securement device may comprise a suture and a suture anchor member to secure uvula 400 to nasopharyngeal side 410 of the soft palate 415. It is understood that in exemplary embodiments, the uvula securement device may comprise a staple, tack, rivet, suture, etc. made of bio-absorbable or non bio-absorbable material Referring now to FIG. 18, curved portion 330 of securement tool is used to position uvula 400 proximal to nasopharyngeal side 410 of the soft palate 415 (e.g., by folding uvula 400 back towards nasopharyngeal side 410). In this embodiment, a suture 530 is coupled to a needle 535 and a suture anchor member 545. Needle 535 can be coupled to actuation member 340 of securement tool 300. As actuation member 340 is moved in the previously-described manner, needle 535 is pushed into soft pallet 415 so that needle 535 pierces the nasopharyngeal side of 410 of the soft pallet 415 and the uvula 400. Actuation member 340 can then be retracted, withdrawing needle 535 from soft palate 415 and uvula 400. Suture anchor member 545 remains in place (as shown in FIG. 19), and suture 530 can be used to secure uvula 400 to nasopharyngeal side of 410 of the soft pallet 415. A suture knot or other securement mechanism (not shown) may be used to secure uvula 400 to nasopharyngeal side of 410 of the soft pallet 415.

While exemplary embodiments are described herein, it will be understood that various modifications to the method and apparatus can be made without departing from the scope of the present invention. For example, different numbers of barbs or extensions may be used. In addition, the initial placement of uvula securement device may be altered from that shown in the exemplary embodiments. Furthermore, the sequential recitation of steps in any claim is not a requirement that the steps be performed in any particular order, unless otherwise so stated.

The invention claimed is:

1. A method of securing a uvula, the method comprising:
providing a securement device;
folding the uvula over towards a nasopharyngeal or oral side of a soft palate so that the uvula is positioned proximal to the side of a soft palate; and
securing the uvula to the nasopharyngeal or oral side of the soft palate with the securement device.

2. The method of claim 1, wherein the uvula is folded towards the nasopharyngeal side of the soft palate.

3. The method of claim 1, wherein the uvula is folded towards the oral side of the soft palate.

4. The method of claim 1, wherein the securement device comprises a barb.

5. The method of claim 1, wherein the securement device comprises a suture and a suture anchor member.

6. The method of claim 1 wherein the securement device is selected from the group consisting of a staple, tack, rivet and suture comprising a bio-absorbable material.

7. The method of claim 1 wherein the securement device is selected from the group consisting of a staple, tack, rivet and suture comprising a material that is not bio-absorbable.

8. The method of claim 1 wherein: securing the uvula to the soft palate with the securement device comprises:
providing an attachment tool comprising:
a first shaft with a first end having a first slot;
a second shaft with a second end; and an actuator configured to move the second end closer to the first end;
placing the securement device in the first slot;
positioning the attachment tool so that the uvula is positioned between the first end and the second end;
actuating the actuator so that the second end engages the uvula and the uvula engages the first end;
actuating the actuator to move the second end away from the first end; and
moving the attachment tool so that the securement device slides out of the first slot.

9. The method of claim 1 wherein: securing the uvula to the soft palate with the securement device comprises:
providing a securement tool comprising a handle, a shaft, and a curved portion distal to the handle;
utilizing the securement tool to position the uvula so that the securement device is proximal to the nasopharyngeal side of the soft palate; and
engaging the curved portion with the uvula and exerting a compressive force on the uvula to secure the securement device to the nasopharyngeal side of the soft palate.

10. The method of claim 1 wherein securing the uvula to the soft palate with the securement device comprises extending an actuation member from the securement device.

11. A method of securing a uvula, the method comprising:
providing a securement device;
engaging the securement device with the uvula;
folding the uvula over towards a nasopharyngeal or oral side of a soft palate so that the uvula is positioned proximal to the soft palate; and
engaging the securement device with soft palate to secure the uvula to the soft palate.

12. The method of claim 11, wherein:
the securement device comprises a central portion having a first side with a first barb; and
securing the securement device to the uvula comprises penetrating the uvula with the first barb.

13. The method of claim 12, wherein securing the securement device to the soft palate comprises penetrating the soft palate with the first barb.

14. The method of claim 12, wherein: the central portion of the securement device comprises a second side with a second barb; and securing the securement device to the soft palate comprises penetrating the soft palate with the second barb.

15. The method of claim 11, wherein the uvula is folded towards the nasopharyngeal side of the soft palate.

16. The method of claim 11, wherein the uvula is folded towards the oral side of the soft palate.

17. The method of claim 11, wherein the securement device engages a posterior portion of the uvula.

18. The method of claim 11, wherein the securement device engages the nasopharyngeal side of the soft palate.

19. The method of claim 1, wherein the securement device initially engages the uvula and subsequently engages the soft palate.

20. The method of claim 11, wherein the securement device initially engages the soft palate and subsequently engages the uvula.

* * * * *